(12) United States Patent
Richards

(10) Patent No.: US 8,470,303 B2
(45) Date of Patent: Jun. 25, 2013

(54) AUTOMATED METHOD AND SYSTEM FOR INTRODUCING MOLECULAR IODINE INTO DRINKING WATER

(76) Inventor: James C. Richards, Sudbury, MA (US)

( * ) Notice: Subject to any disclaimer, the term of this patent is extended or adjusted under 35 U.S.C. 154(b) by 104 days.

(21) Appl. No.: 13/018,955

(22) Filed: Feb. 1, 2011

(65) Prior Publication Data
US 2011/0195033 A1 Aug. 11, 2011

Related U.S. Application Data

(60) Provisional application No. 61/300,630, filed on Feb. 2, 2010.

(51) Int. Cl.
*A61K 8/20* (2006.01)
(52) U.S. Cl.
USPC .............................................. 424/51; 424/292
(58) Field of Classification Search
USPC .................................................. 424/51, 292
See application file for complete search history.

(56) References Cited

U.S. PATENT DOCUMENTS
5,919,374 A * 7/1999 Harvey et al. ................. 210/753

* cited by examiner

*Primary Examiner* — Rei-tsang Shiao
(74) *Attorney, Agent, or Firm* — Clifford Kraft

(57) ABSTRACT

A system and method for delivering molecular iodine or any other substance into a pet's drinking water on a daily basis without exceeding the safe amount allowed for the pet. The present invention delivers a particular amount of molecular iodine into the pet water supply to achieve maximum benefit of $I_2$ to reduce or eliminate bad pet breath and minimize total iodine in the pet diet so that 20-40 μg/mL/Kg/day iodine is consumed for optimum thyroid health. The preferred method is to use a solution created by dissolving iodine crystals in absolute ethanol. The iodine will only be in solution as $I_2$ for a short time as it undergoes out gassing and hydrolysis at neutral pH. The present invention removes the iodine from the drinking water after the pet drinks. Therefore, during the day, pets will get no additional iodine—only fresh water from the water reservoir. Each enrolled pet is recognized by the system using an ID tag such as an RFID tag. This insures that, when there are multiple enrolled pets, each pet receives its specific dose, and only as often as is programmed. Vitamins, drugs and other substances can also be administered to pets using the present invention.

10 Claims, 4 Drawing Sheets

AUTOMATED METHOD AND SYSTEM FOR INTRODUCING MOLECULAR IODINE INTO DRINKING WATER

This application is related to and claims priority from U.S. Provisional Patent application No. 61/300,630 filed Feb. 2, 2010. Application 61/300,630 is hereby incorporated by reference.

BACKGROUND

1. Field of the Invention

The present invention relates generally to the field of pet and human health and more particularly to an automated method for curing bad breath by periodically introducing a safe amount of molecular iodine into drinking water.

2. Description of the Prior Art

It is known in the art that in many circumstances so-called bad oral breath is caused by microbes in the mouth and specifically between the teeth and gum tissue. Some of these microbes produce sulfur-containing compounds that can lead to "rotten-egg" breath and can be very pronounced in animals with periodontal disease.

It is also known in the art to use iodine to disinfect drinking water, and in particular, others have used iodine to disinfect animal drinking water. For example, the system sold under the name of UltraDyne-a™ adds one cap full of its iodine containing formula to 30,000 parts of animal's drinking water resulting in a working solution of 1-5 ppm/mL. This can result in very large amounts of iodine anions along with molecular iodine or "free iodine" being consumed on a daily basis. The amounts added to the water will result in the animals consuming 10-20 times the recommended amount of total iodine for thyroid function and could lead to deleterious outcomes (weight loss, hyperthyroidism, failure to thrive, etc.). Prior art iodine additives use a mixture of iodine compounds including iodides and iodates as well as molecular iodine. This is generally done since molecular iodine dissipates fairly rapidly from water at neutral pH. The iodides and iodates, at a slightly acid pH, continue to produce more molecular iodine.

Harvey et al. in U.S. Pat. No. 5,919,374 teach disinfecting water for farm animals with iodine. Solid iodine is first dissolved in water to produce a saturated iodine species-containing aqueous solution at a pre-selected temperature. This solution is then blended with the drinking water to produce a diluted iodine species bacterium-free aqueous solution. A disadvantage of this method is that generally the water has to be heated to a controlled temperature to dissolve the iodine. Also, Harvey recommends maintaining a fixed amount of iodine concentration in the water continuously. This is a disadvantage because it may lead to particular animals ingesting too much iodine, and because iodine generally leaves a water solution fairly rapidly at room temperature, there may be considerable wasted iodine.

Iodine exists in many forms in aqueous solution at room temperature and neutral pH. These include $I^-$, $I_2$, HOI, $H_2OI^+$, $OI^-$, $I_3^-$, and $I_5^-$. Because $I_2$ is the only anti-infective form of iodine in water at pH below 7 (HOI dominates in water above pH 7) in any of the prior art systems, it would be very advantageous to have a unique system that delivers only molecular iodine ($I_2$) into pet drinking water. Such a method and system will kill oral bacteria responsible for bad breath. In addition, iodine reacts with sulfur containing compounds e.g., hydrogen sulfide responsible for the malodor in pet breath and neutralizes the odor by the reaction between molecular iodine and methyl mercaptan, dimethyl sulfide and hydrogen sulfide, to produce the corresponding sulfonic acids which have substantially reduced odor or sulfur smell.

SUMMARY OF THE INVENTION

The present invention is directed toward a unique system and method for delivering molecular iodine into a pet's drinking water on a daily basis without exceeding the safe amount allowed for the pet. The present invention delivers a particular amount of molecular iodine into the pet water supply to achieve maximum benefit of $I_2$ to reduce or eliminate bad pet breath and minimize total iodine in the pet diet so that 20-40 µg/mL/Kg/day iodine is consumed for optimum thyroid health. The preferred method is to use a solution created by dissolving iodine crystals in absolute ethanol. Molecular iodine is completely soluble in 100% alcohol. The advantage of using iodine in 100% alcohol is that a very small aliquot (0.5 mL into 500 mL water) of 1% iodine (10,000 µg/mL) can be injected into water to achieve instant dissolution and achieve the desired iodine concentration rapidly. The iodine will only be in solution as $I_2$ for a short time as it undergoes out gassing and hydrolysis at neutral pH. Furthermore, the present invention removes iodine from the drinking water after the pet drinks. Therefore, during the day, pets will get no additional iodine—only fresh water from the water reservoir. The present invention delivers optimal amounts of iodine to achieve optimal thyroid health and function in addition to eliminating bad breath. There are several ways to accomplish this; however, a preferred way is to deliver the iodine at the time when pets drink—first in the AM and later in the PM or only one time per 24-hour period. The system will use a radio frequency (Rf) transmitter and receiver-based system specific for each pet. The system will recognize each pet specifically and deliver iodine only at designated times and at designed volumes. At all other times the water system will only deliver pure water. This system disinfects the pet bowl, pet(s) would get antiseptic doses of iodine in the morning and all pets would get iodine for optimum thyroid health and function. The preferred embodiment of the present invention recognizes a particular pet approaching the bowl with an Radio Frequency Identification (RFID) tag. Any pet recognition method is within the scope of the present invention.

It is therefore an object of the present invention to deliver molecular iodine into a pet's drinking water on a daily basis without exceeding the safe amount allowed for the pet.

It is a further object of the invention to deliver a predetermined amount of iodine each day sufficient to disinfect the water and provide the correct amount of iodine needed by the pet.

It is a further object of the invention to deliver molecular iodine into water by using aliquots of pure iodine dissolved in absolute alcohol.

It is a further object of the invention to deliver iodine into drinking water from a disposable canister.

It is an object of some embodiments of the present invention to identify individual pets as they approach a water source so that each pet's iodine intake can be separately monitored.

These and other objects of the present invention will become apparent in the following descriptions and illustrations.

DESCRIPTION OF THE FIGURES

Attention is now directed to several drawings that illustrate features of the present invention.

Several drawings and illustrations have been presented to aid in understanding the present invention. The scope of the present invention is not limited to what is shown in the figures.

DETAILED DESCRIPTION OF THE INVENTION

The present invention is related to a system and method for dispensing molecular iodine in controlled amounts into drinking water, and in particular into a pet's drinking water. The method for curing pet bad breath comprising the steps of (1) sensing the presence of a specific pet followed by (2) precise pump delivery of an aliquot of molecular iodine into (3) a water reservoir followed by pet drinking the immediately iodinated water followed by (4) pet movement away from water reservoir. The pet movement away from the water reservoir produces (5) a signal that switches a valve (6) that passes all water in the water bowl through (7) a filter device that removes remaining iodine from the water bowl and results in a full reservoir of iodine-free water now filtered and purified.

(1) Each pet has a unique signal sending device attached to the pet. A preferred signal sending device is an RFID tag. The signal generated by the device is specifically designed to only be detected when the pet is immediately above the drinking water. (2) Each unique sending device is programmed with the pet identification so that the correct iodine dose will be given once per day per animal. At all other times in a 24-hour period when the pet drinks generally no iodine is injected into the water reservoir. This schedule can be changed for a particular pet if necessary. (3) The iodine is injected into the water and rapidly mixed with the water in a reservoir. (4) When the animal finishes drinking and leaves the water reservoir the signal loss (5) triggers a valve that pumps the remaining iodinated water through a filter to remove remaining iodine and (6) filtered water returns to the reservoir and (7) new water enters the water bowl from the water reservoir to return the water volume to a predetermined amount. The volume of water consumed by any animal is approximately proportional to the animal's weight. Therefore if the molecular iodine concentration in water is 5-10 mcg/mL then the amount of water consumed at a single early AM will supply both sufficient iodine to eliminate pet bad breath, kill oral pathogens and supply sufficient iodine for optimal thyroid health and thyroid hormone maintenance.

Figure 1:
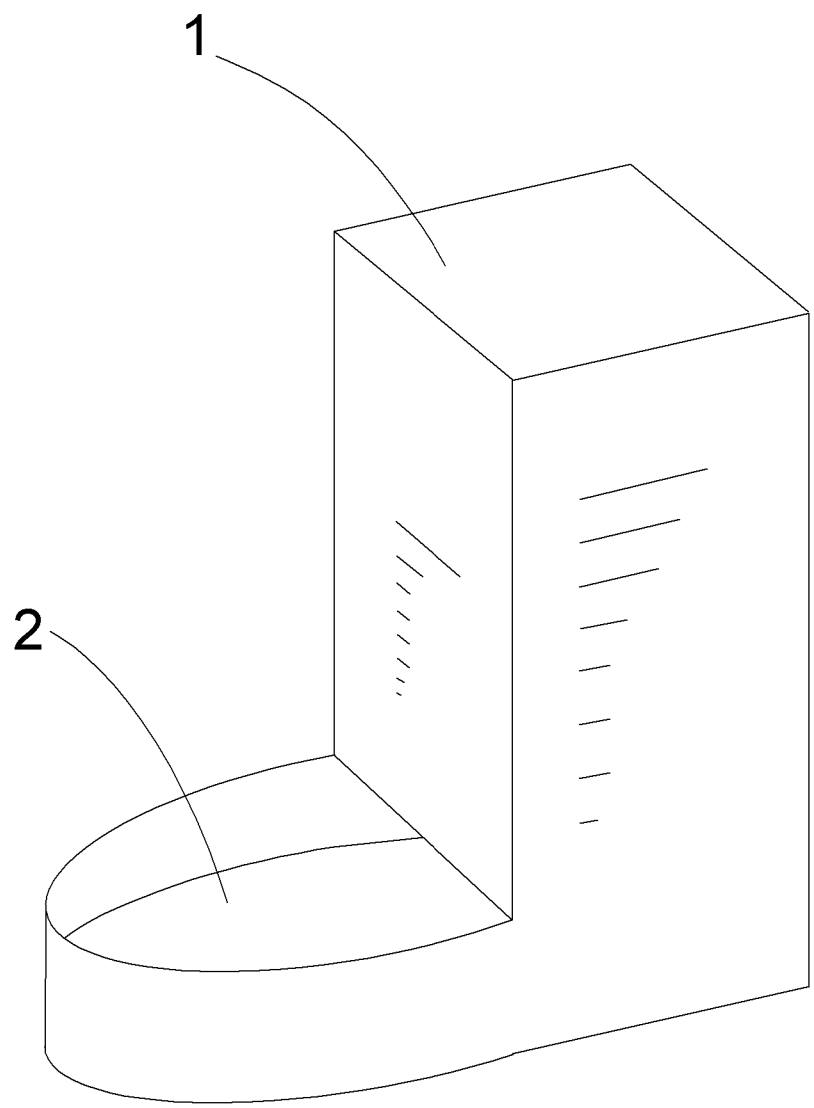
FIG. 1 shows an embodiment of the present invention as a water reservoir and drinking bowl

FIG. 1 shows a perspective view of an embodiment of the present invention. A water reservoir and case 1 with electronic and fluid components is situated above a pet water drinking bowl 2. The case 1 also contains a programmed electronic controller, pumps and a filter.

Figure 2:
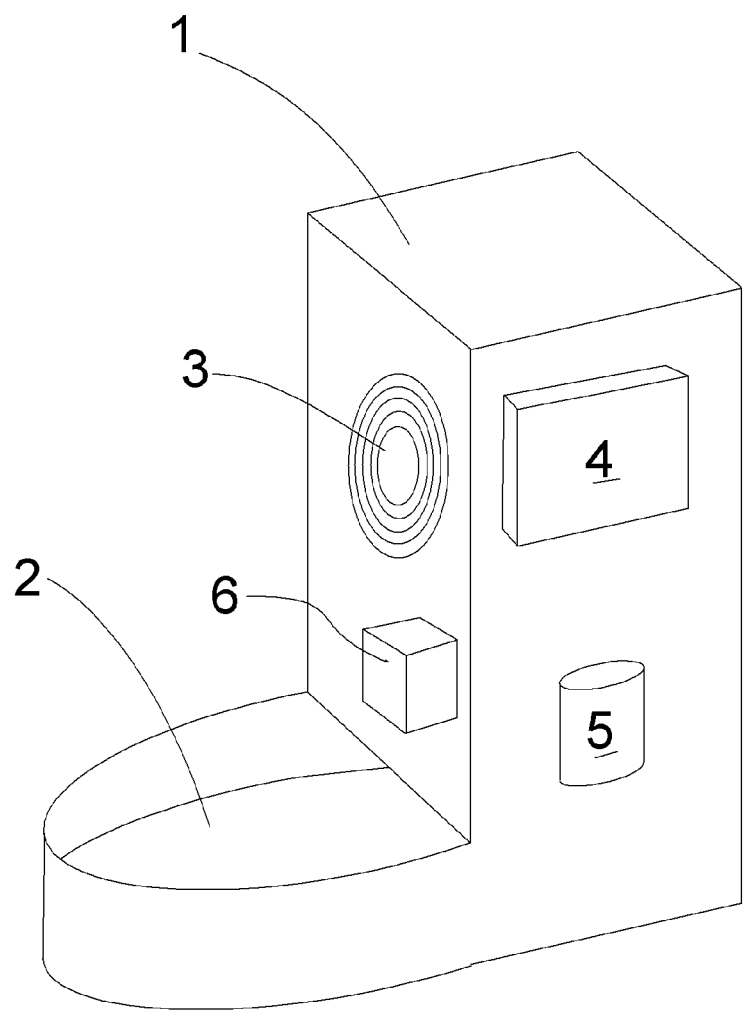
FIG. 2 shows some of the parts included in the present invention.

FIG. 2 is similar to FIG. 1, but shows an RFID tag reader antenna 3, a pump 6, an electronics module 4 and an additive reservoir 5 that generally contains Iodine.

An RF (radio frequency) transmitter/receiver (RFID tag reader) module is attached to processor. Each unique RF module or RFID tag would be attached to a particular pet or animal. Each pet or animal has a unique signature. A water reservoir (contained in 1) is fluidly attached to the water bowl 2. A control circuit board 4 containing the RF detection module and digital circuitry to control the pump and pump valve. Generally, the control circuit board 4 contains a processor. This can be a microprocessor, micro-controller, PC processor, or any other processor. The present invention can also be controlled remotely over the Internet, or remotely from any location either via a network or by radio. The water reservoir and water bowl are typically designed to maintain a constant volume of water (such as 500 mL or any other value) in the water bowl at all times. If the iodine cartridge (which can be disposable) contains 1.0 mg/mL of molecular iodine in 100% ethanol, then the system will inoculate 0.5 mL into the water supply to create a final iodine concentration of 10 mcg/mL in 500 mL water. While this concentration is given by way of example, any other concentration is within the scope of the present invention. When the pet is finished drinking and leaves the bowl area the RF signal will be lost, and the water valve will switch to flush iodine from the bowl. All the remaining iodinated water will pass through the disposable filtration cartridge containing substances that remove iodine from the water and the filtered water is returned to the water bowl. Additional water can then enter the water bowl from the water reservoir to again achieve a final desired volume. When the same pet again comes to the water bowl later in the same 24-hour period the system will not deliver more iodine. This pet will typically not receive more iodine until the next day.

The present invention delivers a predetermined amount of molecular iodine into the pet water supply to achieve maximum benefit of $I_2$ to reduce or eliminate bad pet breath and minimize total iodine in the pet diet so that 20-40 mcg/mL/Kg iodine is consumed for optimum thyroid health. The preferred method is to use a solution created by dissolving iodine crystals in absolute ethanol. Molecular iodine is completely soluble in 100% alcohol. The advantage of using iodine in 100% alcohol is that a very small aliquot of 1% iodine (10,000 mcg/mL) can be injected into water to achieve instant dissolution and achieve the desired iodine concentration rapidly. The iodine will only be in solution as $I_2$ for a short time as it undergoes out gassing and hydrolysis at neutral pH. Therefore, during the day pets will get no additional iodine—only fresh water from the water reservoir. The present invention delivers optimal amounts of iodine to achieve optimal thyroid health and function in addition to eliminating bad breath.

A preferred way of practicing the present invention is as follows: the system can deliver the iodine at time when pets drink—first in the AM and later in the PM or only once per day either in the AM or PM. The system can use a clock to deliver iodine to achieve a concentration in the pet water of 5-10 ppm/mL from e.g., 5-7 AM and later from 5-7 PM. All other times the water system would only deliver pure water. This system disinfects the pet bowl, pet(s) would get antiseptic doses of iodine in the morning and evening and all pets would get iodine for optimum thyroid health and function. No other pet water system disinfects the pet water after the water enters the drinking bowl and maintains a clean bowl as a result.

A typical embodiment of the present invention can include a water reservoir, a clock or timer, an iodine injection cartridge or other mechanism, and a drinking bowl for the pet. Since many facilities have multiple pets, it is advantageous in some embodiments to identify particular pets and control iodine dispensing based on a particular pet. This can be done with a collar RFID tag or other readable identification device. However, one embodiment of the present invention simply dispenses iodine into the water in the morning and evening (or at other particular times) without distinguishing between pets in a household. Normally, all of the pets will drink at these times and receive their required iodine. The bowl will remain clean during the day and night, and at other times, the pets simply receive fresh water.

The following reactions involving iodine should be noted:
(1) $2I^- - 2e \rightarrow I_2$ formation of molecular iodine
(2) $HOI \leftrightarrow H^+ + I^-$ dissociation of hypoiodic acid
(3) $I_2 + H_2O \leftrightarrow HOI + H^+ + I^-$ hydrolysis of molecular iodine
(4) $HOI + H^+ \leftrightarrow H_2OI^+$ protonation of hypoiodic acid
(5) $H_2OI^+ \leftrightarrow HOI + OI^- + H^+$ hydrolysis of iodine cation
(6) $OI^- + I^- + H_2O \leftrightarrow HI_2O^- + OH^-$ iodination of hypoiodite
(7) $I_2 + I^- \leftrightarrow I_3^-$ triiodine formation The only significant anti-infective iodine species in water is molecular iodine ($I_2$). In the pH range of 6.0<->7.0, $I_2$ is favored when $I_2$ is added directly into water. As can be seen from equation (3) $I_2$ will undergo hydrolysis rather rapidly (minutes to hours), and also $I_2$ has low solubility in water at standard temperature and pressure (STP). If the pH of the water is kept at about pH 6.0, $I_2$ is favored, but if the pH is above 7.0, $I_2$ will hydrolyze (3) to $I^-$ and HOI and $I_3^-$ (7) can form and accumulate in the water.

I have determined experimentally that $I_2$ is lost from the water at room temperature at a linear rate of about 0.3 mcg/mL/hour when the pH of the water was adjusted to ~pH5-5.5 with acetic acid to prolong survival of $I_2$ in water. Thus after 24 hours>90% of the $I_2$ is lost either to hydrolysis $I_2 + H_2O \leftrightarrow HOI + H^+ + I^-$ hydrolysis of molecular iodine or volatile $I_2$ via out gassing. At higher pH, the iodine will dissipate faster or be converted to HOI. At neutral pH=7 the I2 loss is ~0.5 mcg/mL/hr so that >90% is gone within 4 hours.

I have also determined experimentally some water consumption rates for pets: I measured the volume of water the test subjects (two 35 kg dogs and two 4 kg cats) consumed over a 24 hour period in four separate experiments and the average daily water consumption was 2.7 liters/24 hours. If we assume water consumption is approximately proportional to animal body weight then the animals were drinking 35 mL water/kg/day. Furthermore, the average $I_2$ concentration was approximately 5 mcg/mL over the 24 hour time period. The amounts are summarized below.

| Subject | Animal Weight (Kg) | Water Consumption (mL/24 hrs) | Iodine Consumption (mcg/mL/24 hr) |
|---|---|---|---|
| Dog 1 | 35 | 1225 | 6125 |
| Dog 2 | 35 | 1225 | 6125 |
| Cat 1 | 4 | 140 | 700 |
| Cat 2 | 4 | 140 | 700 |

The daily recommended dietary iodine dose is 20-40 mcg/Kg in humans. It is generally recognized that the daily dog/cat iodine thyroid iodine requirement would be approximately the same as the adult human daily iodine requirement and the daily adult human iodine requirement is 20-40 mcg/Kg/day. Therefore, the dog test subjects should consume between 700-1400 mcg $I_2$/day and the cat test subjects should consume 80-160 mcg $I_2$/day.

The conclusion from these studies is that these animal pet subjects consumed 4.35->8.75 times the daily-recommended dosage of iodine. There were no obvious changes in pet behavior, food consumption or excretion However, they were followed for only 4 days. Later, they were followed for 3 weeks with I2 at 1-5 mcg/mL and no ill effects were noted.

In order to keep charged iodine species in the water from rising too high, particular embodiments of the invention can include a mixed bed resin in a filtration cartridge to remove only charged ions e.g., $I^-$, $I_3^-$, $OI^-$ and $H_2OI^-$. Uncharged $I_2$ passes through the filtration cartridge and will also maintain antisepsis for the entire cartridge. The primary reason for removing the charged ions is that even though do not contribute to antisepsis or disinfection, they nevertheless contribute to the total amount of iodine in the pet's body and could lead to excessive iodination of thyroid and possibly lead to hyperthyroidism. Activated charcoal and mixed bed resin will be included in the filtration device to remove all or most of the iodine forms.

Various compositions of the iodine solution can be used in the present invention in the form of a disposable cartridge with the preferred being simply iodine crystals dissolved in absolute alcohol. While commercial tincture of iodine might be used as a source of $I_2$, tincture of iodine is more precisely termed "Iodine Tincture USP" and contains 2% iodine, 2.4% iodide and 47% alcohol. The potential problem with this iodine source is that more than half of the total iodine is iodide ($I^-$) and serves no use in present invention other than provide unnecessary added iodine to the pet total body iodine concentration.

As stated, one embodiment uses solid iodine crystals in 100% ethanol (absolute ethanol). A possible 10% stock solution of $I_2$ in 100% ethanol can be prepared by dissolving 1 gram of solid iodine in 10 mL of 100% ethanol (100 mg/mL). A 1% iodine solution can be prepared in 100% ethanol using a 1:10 dilution of the stock or 10 mg/mL. This results in 10,000 ppm/mL in ethanol.

As previously stated, one embodiment of the invention simply dispenses a predetermined amount of iodine into the pet drinking water at particular times during the day (morning and evening for example) without distinguishing between particular pets. A more complex embodiment can detect a particular pet approaching the bowl using an RFID tag or other wireless device on the pet collar.

The activation of iodine delivery to water is based on system sensing of the pet presence. One concept is a simple proximity sensor. Once the pet is near the dish the system is activated and fresh iodinated water is pumped into the bowl. This can be accomplished with either motion sensors or sensors on the pet collar. Another concept is that each pet has a microchip on the pet collar that identifies each pet. In addition the system can detect which pet is about to drink water and inject iodine into the system appropriate for each pet. For example, if a pet drank a lot of water on a hot day the system will know approximately how much iodinated water the pet had consumed during the day. A safe daily iodine intake for mammals including man is 20-40 mg/Kg body weights per 24 hr period. This range can be programmed for each pet and stored so the system knows how much iodinated water each pet receives. Therefore, the system micro chip identity collar will permit regulation of the dietary iodine intake, measure the amount of water consumed daily and permit storing of pet water consumption including wireless access when owners are traveling to provide peace of mind as to pet safety. It should be pointed out that the pet microchip collar system could easily be used with a food dispensing system.

As stated, in the preferred embodiment of the present invention, iodine can be injected in the morning and/or evening. Then, after the pet drinks (or pets drink), the iodine can be removed by the filter.

A processor with a timer can control a valve to allow predetermined amounts of iodine to be injected into the drinking water at particular times of the day. The processor may be a microprocessor, microcontroller or personal computer, or it may simply be a logic circuit that performs the function. If it is a processor, it can also be equipped with volatile and non-volatile memory as is known in the art. The processor can also control the pump The pump while preferably a small electric pump can be any type of pressure generating system. The timer may be a time-of-day clock or a simple counter. Any types of pumps, timers or processors are within the scope of the present invention. As mentioned, a wireless transponder may be used to identify a particular pet. This may be an RFID transponder known in the art, or it may be any other type of wireless system for communicating with a pet collar or pet implant chip. The preferred method is to use an RFID tag on the pet collar with the transponder being an RFID transponder or receiver.

Figure 3:
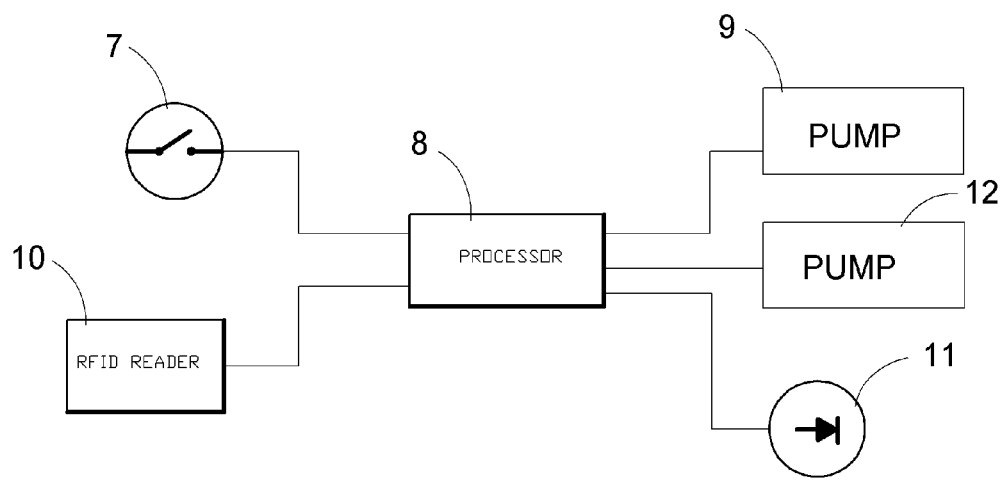
FIG. 3 shows an electrical block diagram of an embodiment of the present invention.

FIG. 3 shows a block diagram of a basic embodiment of the present invention. User inputs 7 are put into software executing in the processor 8. These can include the exact dose and frequency of dosing for each pet registered into the system. A new pet can be entered, and an old pet removed. Enrollment can consist of entering an identifier for the pet and then presenting its RFID collar to the RFID reader 10.

When an enrolled pet approaches the RFID reader 10, its particular tag is read and identified. The processor can then determine if a dose should be administered. If a dose is to be administered, one of the additive (iodine) pumps 9, 12 can inject an exact amount of iodine solution into the bowl. When the pet leaves, the processor 8 can command a circulation pump (not shown) to activate and remove the water containing iodine, preferably through replaceable filter canister. An alternative is to simply eject the iodine containing water into a drain or holding tank. A LED 11 can indicate when iodine is being administered to a pet or alternatively when an enrolled pet has been detected.

Figure 4:
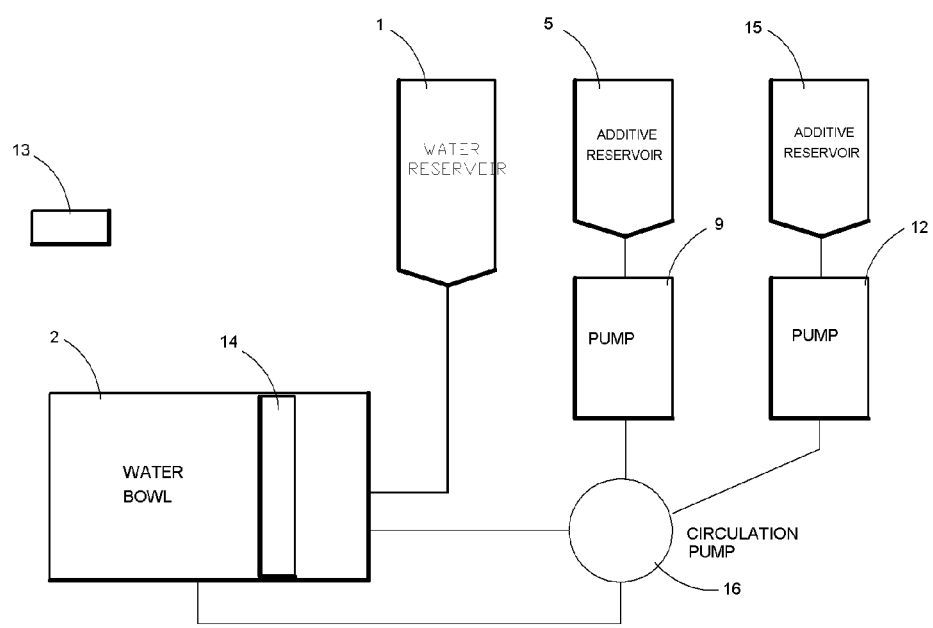
FIG. 4 shows a fluid block diagram of an embodiment of the present invention.

FIG. 4 shows a fluid diagram of a preferred embodiment of the present invention. The water bowl 2 is connected to the water reservoir in the case 1. A filter canister 14 can remove iodine when a circulation pump 16 is activated. Additive pumps 9 and 12 can administer iodine from additive reservoirs 5 and 15 respectively. As previously noted, other additives besides iodine may be desirable such as vitamins or even prescription drugs. In this case, one of the additive reservoirs can contain iodine and the other can contain any other substance. In one embodiment of the present invention, the invention is not used to administer iodine, but rather up to two additives of any type. The processor can be programmed for any type of substance administration, and any type of substance administration is within the scope of the present invention.

In summary, the present invention can supply antiseptic anti-infective iodine or other substances into pet drinking water so that several important events occur:
1. Offensive pet breath is eliminated and in fact is virtually odorless.
2. Optimal thyroid health is promoted by guaranteeing optimal iodination of the thyroid gland.
3. The pet water supply stays clean and fresh at all times and there is no microbial growth or bio-film/slime in the dish.
4. Antiseptic iodine will inhibit progression of periodontal disease and cat stomatitis.
5. Oral mucosal wounds will be disinfected.
6. Pet water consumption will be monitored and recorded for owner peace of mind.

Prior art systems have not used iodine to prevent pet breath because: most people consider PVP-iodine or Betadine to be the primary form of iodine disinfectant. PVP-iodine is 10% total iodine. Of all iodine species in 10% PVP-iodine only 2-3 ppm/mL is $I_2$. PVP-iodine is not acceptable as a treatment for water disinfection or any oral antisepsis. Only $I_2$ is anti-infective. If anyone would add $I_2$/free molecular iodine to an open dish of water they would discover that all $I_2$ is gone from the system with in several hours. $I_2$ is poorly soluble in water and will "de-gas" rapidly form a water suspension. This means that $I_2$ will leave as a gas very rapidly. It has not been appreciated in the prior art that pure $I_2$ can be added to a water source and provide a constant antiseptic concentration of molecular iodine exactly when the pet drinks and fills the oral cavity with anti-infective iodine and thereby kills oral bacteria responsible for "bad breath".

Others have previously recognized that pet water bowls are contaminated with bacteria and a source of potentially hazardous bacteria, fungi or viruses. All pet water systems that use filtration systems filter the water before the water enters the pet bowl. Such systems remove antimicrobial chlorine and thus make the water vulnerable to microbial growth. The present invention filters the water after it enters the pet bowl and by adding molecular iodine ($I_2$) into the water, prevents microbial growth in the pet bowl and maintains a clean healthy water supply.

It should be noted that the same compounds that cause bad breath in animals also are present in humans. The system of the present invention can be adapted to provide drinking water for humans that have the same beneficial effects for humans, namely eliminating bad breath and providing a source of daily iodine intake.

It should also be noted that the present invention can be used with any animal, pet or wild, and can be used with humans including human children.

Several descriptions and illustrations have been presented to aid in understanding the features of the present invention. One skilled in the art will realize that numerous changes and variations can be made without departing from the spirit of the present invention. Each of these changes and variations is within the scope of the present invention.

I claim:

1. A method for injecting molecular iodine into a pet's drinking water comprising: injecting molecular iodine into a source of pets drinking water when a pet approaches said source to drink.

2. The method of claim 1 wherein said iodine is dissolved in absolute alcohol.

3. The method of claim 1 wherein a particular pet is recognized by an RFID tag.

4. The method of claim 1 wherein iodine is injected only once a day for a particular enrolled pet.

5. The method of claim 1 wherein iodine is removed from said source of drinking water after said pet leaves said source.

6. A method for injecting molecular iodine into a pet's drinking water comprising:
   injecting molecular iodine into a source of a pet's drinking water when the pet approaches said source to drink;
   removing the iodine from said source of drinking water after the pet leaves said source.

7. The method of claim 6 wherein said iodine is dissolved in absolute alcohol.

8. The method of claim 7 wherein iodine is injected only once a day for a particular enrolled pet.

9. The method of claim 8 wherein a particular pet is recognized by an electronic tag.

10. The method of claim 9 wherein said electronic tag is an RFID tag.

* * * * *